(12) United States Patent
Van Oort

(10) Patent No.: US 7,792,584 B2
(45) Date of Patent: Sep. 7, 2010

(54) SYSTEM AND METHOD FOR CHARACTERIZATION OF ATRIAL WALL USING DIGITAL SIGNAL PROCESSING

(75) Inventor: Geeske Van Oort, Velp (NL)

(73) Assignee: Medtronic, Inc., Minneapolis, MN (US)

( * ) Notice: Subject to any disclaimer, the term of this patent is extended or adjusted under 35 U.S.C. 154(b) by 559 days.

(21) Appl. No.: 11/380,113

(22) Filed: Apr. 25, 2006

(65) Prior Publication Data

US 2007/0250129 A1 Oct. 25, 2007

(51) Int. Cl.
 *A61B 5/0452* (2006.01)
(52) U.S. Cl. .................. 607/26; 600/509; 600/510; 607/28
(58) Field of Classification Search ........... 600/300, 600/515, 510, 517, 518; 607/9, 14, 20, 27, 607/28, 116, 122, 26
See application file for complete search history.

(56) References Cited

U.S. PATENT DOCUMENTS

| | | | |
|---|---|---|---|
| 4,343,312 A | | 8/1982 | Cals et al. |
| 5,425,749 A | * | 6/1995 | Adams .......................... 607/5 |
| 5,601,615 A | | 2/1997 | Markowitz et al. |
| 5,800,470 A | * | 9/1998 | Stein et al. .................... 607/20 |
| 5,921,940 A | * | 7/1999 | Verrier et al. ............... 600/518 |
| 6,029,087 A | | 2/2000 | Wohlgemuth |
| 6,052,621 A | * | 4/2000 | Begemann et al. ........... 607/28 |
| 6,067,472 A | | 5/2000 | Vonk et al. |
| 6,128,526 A | * | 10/2000 | Stadler et al. ............... 600/517 |
| 6,249,702 B1 | | 6/2001 | Van Oort |
| 6,473,647 B1 | * | 10/2002 | Bradley ........................ 607/27 |
| 6,546,292 B1 | * | 4/2003 | Steinhaus et al. ........... 607/116 |
| 6,694,188 B1 | * | 2/2004 | Kroll ............................ 607/14 |
| 6,823,213 B1 | * | 11/2004 | Norris et al. .................... 607/9 |
| 2002/0055764 A1 | * | 5/2002 | Malonek et al. ............. 607/122 |
| 2002/0143265 A1 | * | 10/2002 | Ackerman et al. .......... 600/515 |
| 2002/0183636 A1 | * | 12/2002 | Struble ........................ 600/510 |
| 2003/0195580 A1 | * | 10/2003 | Bradley et al. ................ 607/28 |

(Continued)

FOREIGN PATENT DOCUMENTS

EP 1050271 A 11/2000

(Continued)

OTHER PUBLICATIONS

Navas; "Atrial Fibrillation: Part 1", Nursing Standard, 17, 37, 45-54 (2003).

(Continued)

*Primary Examiner*—Carl H Layno
*Assistant Examiner*—Luther G Behringer
(74) *Attorney, Agent, or Firm*—Michael C. Soldner

(57) ABSTRACT

A system and method for characterizing the atrial wall of the heart is provided. The characterization of the atrial wall can be used for a variety of diagnostic and therapeutic purposes. For example, it can be used to detect precursors to various types of hear disease, such as atrial fibrillation. In one embodiment, the system and method is used to determine a likelihood of fibrosis in the atrial wall. Furthermore, the system and method can detect changes in atrial wall fibrosis that can indicate a continuing degradation in the atrial wall health and an increasing likelihood of atrial fibrillation. In another embodiment, the system and method is used to determine if electrical instability exists in the atrial wall.

12 Claims, 7 Drawing Sheets

U.S. PATENT DOCUMENTS

| | | | |
|---|---|---|---|
| 2004/0059203 A1* | 3/2004 | Guerrero et al. | 600/300 |
| 2004/0167580 A1* | 8/2004 | Mann et al. | 607/17 |
| 2004/0215238 A1* | 10/2004 | van Dam et al. | 607/4 |
| 2005/0043766 A1* | 2/2005 | Soykan et al. | 607/9 |

FOREIGN PATENT DOCUMENTS

| WO | WO 2007/127534 | * 11/2007 |
|---|---|---|

OTHER PUBLICATIONS

Ramanna et al.; "Identification of the Substrate of Atrial Vulnerability in Patients with Idiopathic Atrial Fibrillation", Circulation, 995-1001 (Mar. 7, 2000).

Rostock, et al.; "High-Density Activation Mapping of Fractionated Electrograms in the Atria of Patients with Paroxysmal Atrial Fibrillation," Head Rhythm, vol. 3, No. 1 (Jan. 2006).

Centurion O A et al: "Different distribution of abnormal endocardial electrograms within the right atrium in petients with sick sinus syndrome." British Heart Journal, Dec. 1992, vol. 68, No. 6, pp. 596-600, XP002473472.

Spach M S et al: "Relating extracellular potentials and their derivatives to anisotropic propagation at a microscopic level in human cardiac muscle. Evidence for electrical uncoupling of side-to-side fiber connections with increasing age." Ciculation Research, Mar. 1986, vol. 58, No. 3, pp. 356-371, XP002473473.

International Search Report, PCT/US2007/064051, Nov. 6, 2008, 8 pages.

* cited by examiner

SYSTEM AND METHOD FOR CHARACTERIZATION OF ATRIAL WALL USING DIGITAL SIGNAL PROCESSING

TECHNICAL FIELD

The present invention relates generally to cardiac monitoring. More particularly, the present invention relates to systems and methods for characterization of atrial wall.

BACKGROUND

Cardiac disease continues to be a very serious medical problem affecting large numbers of people. One common type of cardiac problem is atrial fibrillation. Normally, the heart contracts and relaxes to a regular beat. In atrial fibrillation, the heart beats rapidly, with an irregular beat. Atrial fibrillation can have many causes. For example, hypertension, fatigue and infection can lead to atrial fibrillation. As with many other diseases, early detection of cardiac disease is extremely important.

Some types of cardiac disease have known precursors that can be used to determine a future likelihood of illness. For example, one precursor of atrial fibrillation is fibrosis in the atrial wall of the heart. Fibrosis is, in general, the formation of fibrous, scar like tissue. When a scar tissue is formed in the atrial wall, it can lead to variety of cardiac problems, including atrial fibrillation.

Another precursor of atrial fibrillation is electrical instability in the atrial wall. Electrical instability in the atrial wall can lead to a shortened refractory periods, which in turn are a precursor to atrial fibrillation.

Because fibrosis and electrical instability in the atrial wall can lead to cardiac disease, characterization of the atrial wall that can detect these conditions is highly desirable. Thus, there is a continuing need for improved systems and method for characterizing the health of atrial walls in the heart.

BRIEF SUMMARY

The present invention provides a system and method for characterizing the atrial wall of the heart. The characterization of the atrial wall can be used for a variety of diagnostic and therapeutic purposes. For example, it can be used to detect precursors to various types of heart disease, such as atrial fibrillation. In one embodiment, the system and method is used to determine a likelihood of fibrosis in the atrial wall. Furthermore, the system and method can detect changes in atrial wall fibrosis that can indicate a continuing degradation in the atrial wall health and an increasing likelihood of atrial fibrillation. In another embodiment, the system and method is used to determine if electrical instability exists in the atrial wall.

The system and method uses an implantable cardiac device to measure cardiac waveforms in the atrial wall, and uses digital signal processing to characterize the health of atrial wall based on those waveforms. The implantable cardiac device includes one or more electrodes in or near the heart. The electrodes capture cardiac waveforms and the implantable cardiac device samples the waveforms, and analyzes the sampled waveforms using digital signal processing.

In one specific embodiment, the implantable cardiac device evaluates the waveforms by defining an analysis window in the waveforms, and determining the amount of fragmentation in the window. For example, the amount of fragmentation is calculated by determining the number of peaks in the window. Alternatively, the number of zero crossings in the window can be determined. In either case, the implantable medical device evaluates the waveforms and determines the amount of fragmentation in waveforms. The amount of fragmentation in the waveforms can then be correlated to the amount of fibrosis in the atrial wall. In other embodiments, the amount of waveform fragmentation changing over time is tracked. The change in waveform fragmentation can then be used to determine when fibrosis in the atrial wall is increasing.

In another specific embodiment, the implantable cardiac device evaluates the waveforms to determine if electrical instability exists in the atrial wall. For example, to detect a shortening of the refractory period that can lead to an increasing likelihood of atrial fibrillation. The refractory period can be determined by detecting the atrial T-wave and using the atrial T-wave to measure the length of refractory period. As another example, by detecting the atrial impulse response. In this example, a train of pulses is delivered to atrium. Capture of the pulses is determined, and used to calculate the refractory period. In both these examples the atrium wall is characterized by determining the length of the refractory period in the atrial wall.

Thus, the present invention provides system and method for characterizing the atrial wall of the heart to determine if precursors of atrial fibrillation are present.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

A wide variety of implantable cardiac devices are available to treat a variety of cardiac conditions. For example, implantable pulse generators (IPGs) are a type of cardiac device that is generally used to elevate the heart rate that is beating too slowly. This type of device is sometimes referred to as a Bradycardia device or a pacemaker. Another type of implantable cardiac device is an implantable cardiac defibrillator (ICD). This type of device, is generally used to provide burst pacing pulses or a defibrillation shock to the heart when the heart goes into fibrillation. Another type of device is a cardiac resynchronization device (CRT) used in heart failure patients.

The present invention provides a system and method for characterizing the atrial wall of the heart. The characterization of the atrial wall can be used for a variety of diagnostic and therapeutic purposes. For example, it can be used to detect precursors to various types of hear disease, such as atrial fibrillation. In one embodiment, the system and method is used to determine a likelihood of fibrosis in the atrial wall. Furthermore, the system and method can detect changes in atrial wall fibrosis that can indicate a continuing degradation in the atrial wall health and an increasing likelihood of atrial fibrillation. In another embodiment, the system and method is used to determine if electrical instability exists in the atrial wall.

The system and method uses an implantable cardiac device to measure cardiac waveforms in the atrial wall, and uses digital signal processing to characterize the health of atrial wall based on those waveforms. The implantable cardiac device includes one ore more electrodes in the heart. Alternatively, this may also be done using a subcutaneous monitoring device with electrodes located on the device, where the device is placed such that it can detect the relevant signals. In either case the electrodes capture cardiac waveforms and the implantable cardiac device samples the waveforms, and analyzes the sampled waveforms using digital signal processing.

Figure 1:
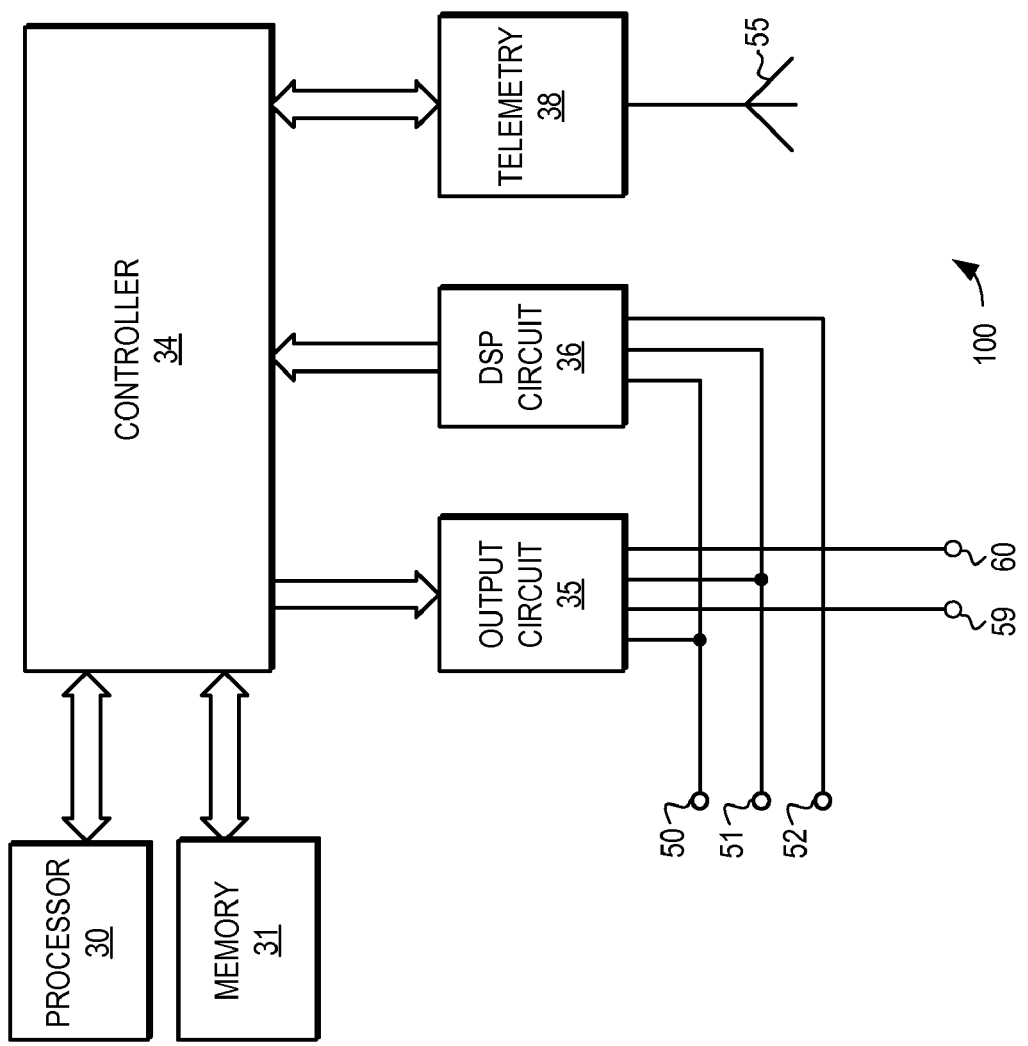
FIG. 1 is a schematic view implantable cardiac device in accordance with an embodiment of the invention.

Referring now to FIG. 1, a simplified functional block diagram of an implantable cardiac device 100 is illustrated. The implantable cardiac device 100 is an example of the type of devices in which the present invention can be implemented. Accordingly, FIG. 1 is considered to be exemplary rather than limiting with regard to the present invention. It should be noted the implantable cardiac device could be implemented as a wide variety of devices, including pacemakers, defibrillators, etc. Further, the implantable cardiac device 100 can be applied to single chamber, dual chamber and multi-chamber systems.

The elements of the apparatus illustrated in FIG. 1 are microprocessor 30, memory 32, a digital controller 34, output circuit 35, a digital signal processing (DSP) circuit 36, and a telemetry/programming unit 38. Memory 31 can include read only memory, typically used to store the basic programming for the device, including the primary instructions set defining the computations performed to derive the various timing intervals performed by the device. Memory 31 can also include random access memory, typically used to store the values of variable control parameters, such as programmed pacing rate, pulse widths, pulse amplitudes, and so forth, which are programmed into the device by the physician.

Controller 34 performs the basic timing and control functions of the implantable medical device. Controller 34 would typically include at least one programmable timing counter, e.g., initiated on paced or sensed ventricular contractions, for timing out intervals thereafter. This timing counter is used to define the escape intervals for timing generation of pace pulses, as well as for timing the respective durations of the charge and recharge pulse portions of triphasic pulses. Controller 34 triggers output pulses to be generated and delivered from output stage 35, and it generates interrupts for waking microprocessor 30 from its sleep state to allow it to perform the required functions. The output circuit 35 is coupled to electrodes 50 and 51 which are employed both for delivery of pulses and for sensing of cardiac signals. Electrode 50 is typically located on the distal tip end of an endocardial lead, and for ventricular pacing is preferably placed in the apex of the right ventricle; for atrial pacing, of course, it is placed in the patient's atrium. Electrode 51 is typically a ring electrode, as used with a bipolar lead. Electrode 52 represents the device housing, which may be used as the indifferent electrode for selected unipolar pacing and/or sensing operations. Of course, for a dual or multi-chamber pacing system, additional electrodes are employed. For example, electrodes 59 and 60 may be used for pacing and sensing in the atrium, while electrodes 50 and 51 are used in the ventricle. Output circuit 35 is controlled by controller 34 to determine the amplitude and pulse width of the pulse to be delivered and to determine which electrode pair is to be employed to deliver the pulse. It should be noted that in some cases the electrodes 51 and 52 would be co-located on the device itself instead of being attached using leads. For example, in subcutaneous cardiac monitoring devices.

Cardiac signals are sensed at a desired pair or pairs of electrodes. For example, bipolar and/or unipolar sensing may be used. In one embodiment, a unipolar lead in the atrium and a unipolar lead in the ventricle are used, e.g., the signals are picked up at electrodes 50 and 59. Sense signals are inputted to DSP circuit 36, which comprises a number of signal processing channels corresponding to signals of interest. For example, in a dual chamber pacemaker which incorporates P wave processing either for rate control, capture detection or any other reason, there would preferably be three channels for respective signal processing of the P, R and T waves. The data resulting from the digital signal processing is transmitted via a bus through controller 34 to processor 30, for the signal classification operations, as well as any other necessary calculations. External control of the implanted device is accomplished via telemetry/control block 38, which allows communication between the implanted device and an external programmer (not shown) via antenna 55.

Figure 2:
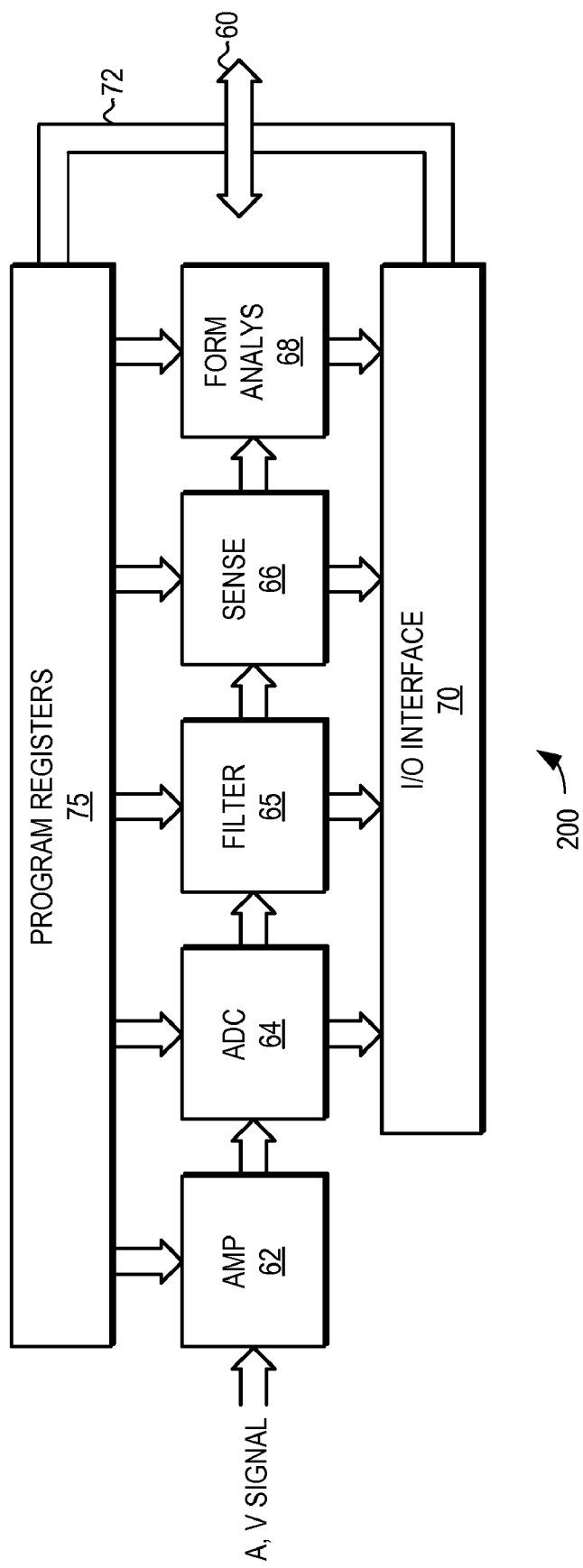
FIG. 2 is a schematic view DSP channel in accordance with an embodiment of the invention.

Turning now to FIG. 2, a block diagram representing the primary components of an exemplary DSP circuit 200 is illustrated. The DSP circuit 200 is exemplary of the type of DSP devices that can be used to implement the present invention. The DSP circuit 200 illustrates a typical DSP channel that can be used to process received signals. It should be noted that this is a simplified example, and that typical DSP devices would suitably include a plurality of DSP channels used for signal processing of respective signals.

The DSP circuit 200 receives a waveform signal, typically an atrial (A) or ventricular (V) signal and processes signal. The received signal is first processed through an amplifier 62. The amplified analog signal is passed into A/D converter 64, for sampling and generation of a corresponding digital signal. The A/D conversion is done by any suitable technique, such as with a delta-sigma modulator. The resulting digital signal from ADC 64 is passed to filter 65 which is suitably a digital bandpass filter having a characteristic to eliminate low frequency signal components and the offset of the converter, as well as to take out high frequency artifacts. The output of filter 65 is connected to sense block 66. Sense block 66 processes the filtered digital signal (referred to herein as SIG) to obtain the slew rate, or slope of the signal, also hereafter referred to as the SL signal, and then compares both the SIG and SL signals to plus and minus threshold voltages to derive a "sense" signal.

Figure 3:
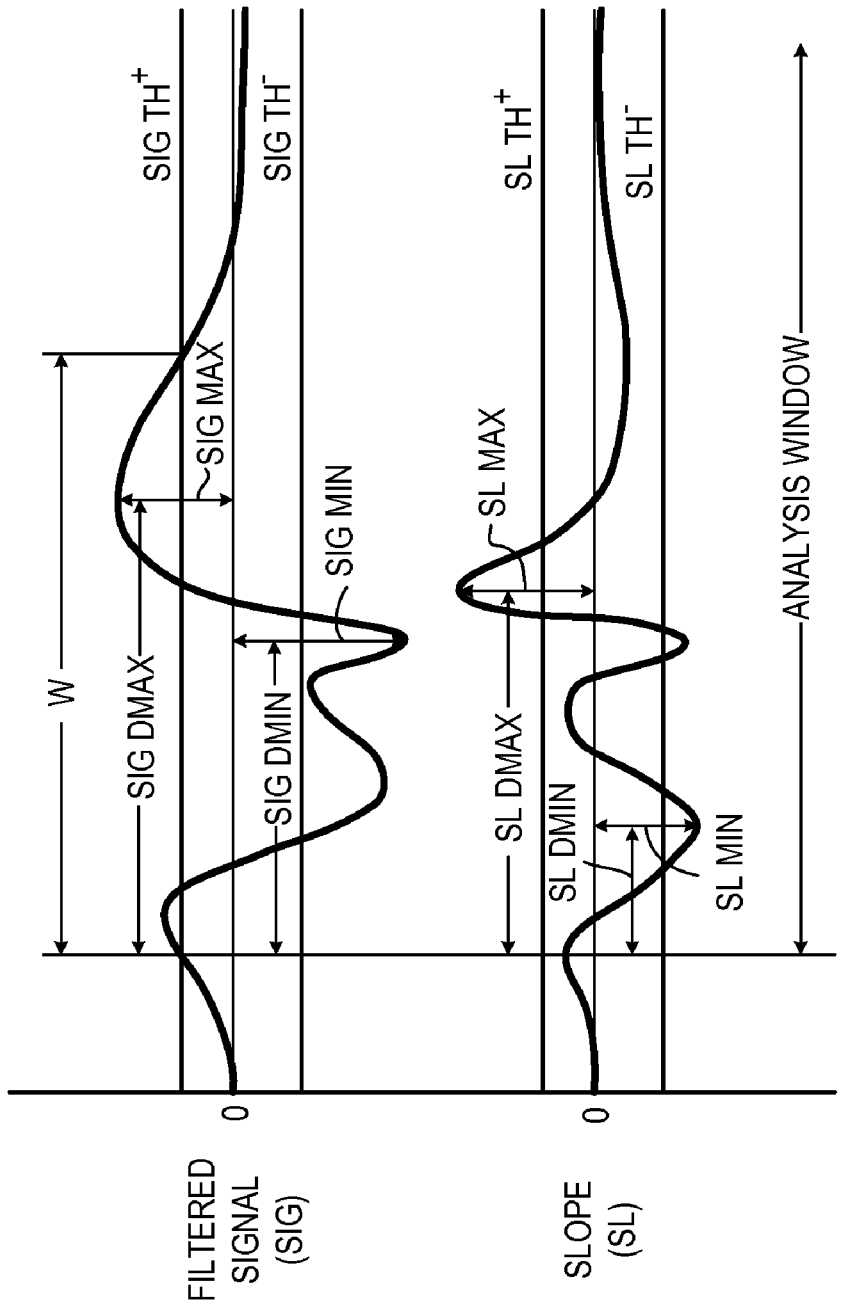
FIG. 3 is a graphical representation of a filtered signal and a filtered signal slope in accordance with one embodiment of the invention.

The "sense" signal is passed to the form analysis block 68. This block is where the DSP circuitry operates to extract parameters from the signal under examination. The parameters extracted from the waveform would typically depend on the specifics of the DSP implementation. As one example, the DSP implementation can extract nine morphological parameters, including the minimum amplitude and maximum amplitude of both the filtered cardiac signal and the slope of the filtered cardiac signal, the time from the start of the analysis window to those four amplitudes, and the signal width from the first threshold crossing to the last threshold crossing. Turning now to FIG. 3, an example of these extracted parameters are illustrated in sample waveforms. FIG. 3 shows a graph of the filtered signal (SIG) and a graph of the slope of the filtered signal (SL). The SIG and SL values in an analysis window defined by the analysis block 68 are analyzed to obtain the signal parameters that are illustrated in FIG. 3. As illustrated in FIG. 3, both maximum and minimum values of SIG during the analysis window are obtained; the positive value is indicated as SIG MAX and the negative as SIG MIN. The time from sense to SIG MAX is indicated as SIG DMAX; and the time from sense to SIG MIN is indicated as SIG DMIN. Likewise, referring to the SL waveform, values of SL MAX and SL MIN are determined, and the time from sense to each is found, namely SL DMAX and SL DMIN. Additionally, the time from first crossing of a threshold to the last crossing of a threshold is determined as labeled W; in this example W is from the first SIG crossing of the positive threshold to the last SIG crossing of the SIG positive threshold.

When the parameters are determined, they are written into the corresponding registers 75. Thus, the parameters are obtained by the DSP circuitry form by continuous operation on each byte of data from the time of the first threshold crossing until the end of the analysis window. The parameters are provided on data bus 60 using the I/O interface 70. The database 60 communicates controller and/or microprocessor in the implantable medical device. For more exemplary information on how DSP can be implemented in such a device, see U.S. Pat. No. 6,029,087 to Werner Peter Wohlgemuth, entitled "Cardiac Pacing System with Improved Physiological Event Classification Based on DSP", which is herein incorporated by reference in its entirety.

As described above, the embodiments of the present invention provides the ability to characterize the atrial wall of the heart that can be implemented using DSP techniques in an implantable medical device. In one embodiment, the system and method is used to determine a likelihood of fibrosis in the atrial wall. Specifically, the implantable cardiac device evaluates the waveforms by sampling the waveforms, defining an analysis window in the sampled waveforms, and determining the amount of fragmentation in the window.

Figure 4:
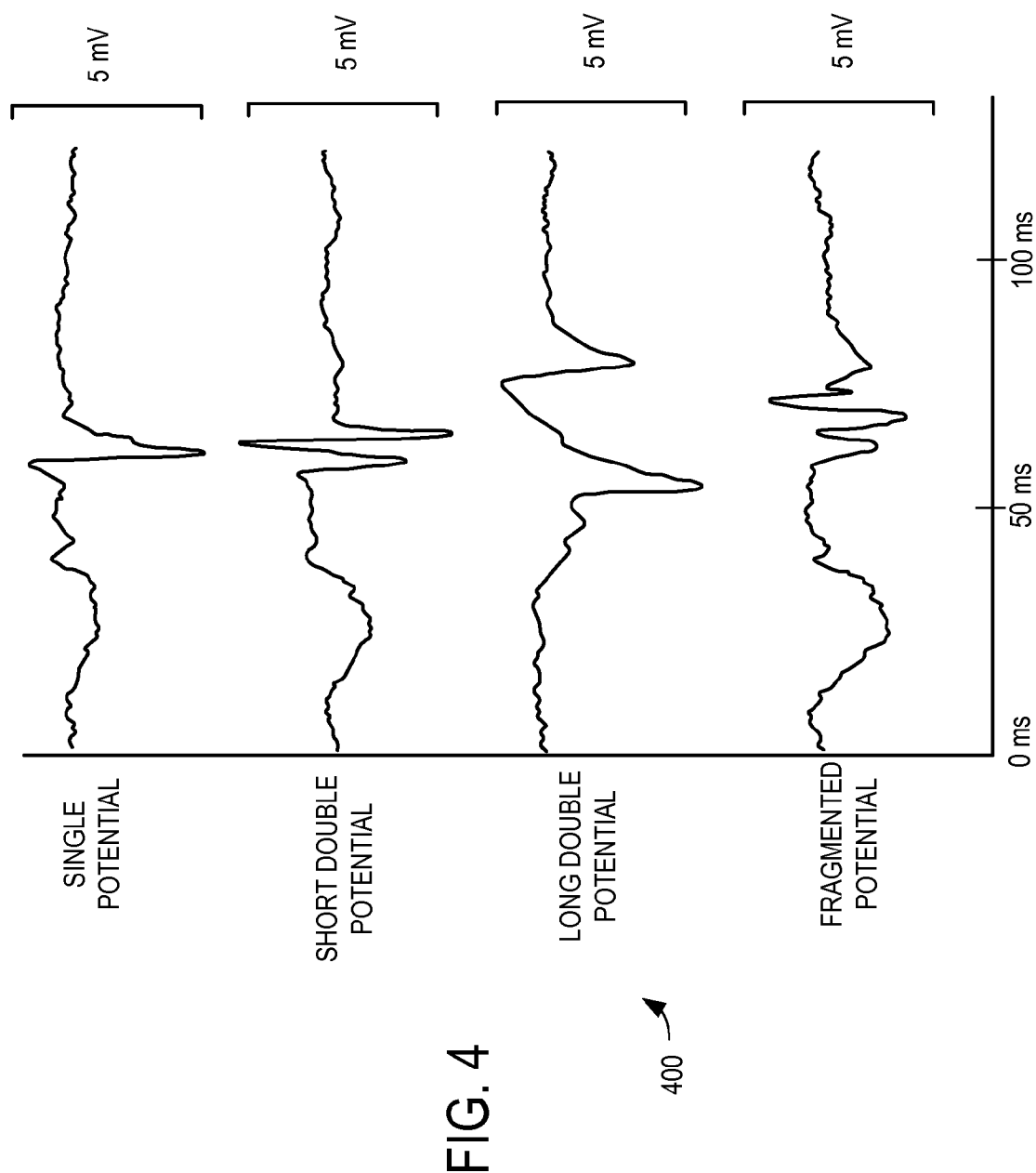
FIG. 4 is a graphical representation of a exemplary atrial electrograms.

Turning now to FIG. 4, a graph 400 illustrates four exemplary waveforms that each illustrate a cardiac electrogram with different a morphology. Specifically, the four cardiac electrograms show a single potential, short double potential, a long double potential and a fragmented potential morphology. An electrogram with a fragmented potential is defined as one with multiple peaks in a window. As can be seen, electrograms showing fragmented potentials have been found to be indicative of fibroses in the atrial wall, which itself may be a precursor to atrial fibrillation.

In the embodiments of the present invention the amount of fragmentation is determined by digital signal processing techniques. Specifically, the implantable cardiac device measures the waveforms in the heart using the appropriate electrodes. Using the DSP techniques described above, an analysis window in the waveform is defined and the waveform is analyzed to determine the amount of fragmentation in the window.

In one embodiment, the amount of fragmentation is calculated by determining the number of peaks in the window. Alternatively, the number of zero crossings in the window can be determined. In either case, the implantable medical device evaluates the waveforms and determines the amount of fragmentation in waveforms. The amount of fragmentation in the waveforms can then be correlated to the amount of fibrosis in the atrial wall. For example, the number of peaks or zero crossings can be used to define a level of fibrosis, which is then compared to threshold values. In a third embodiment, the time from first crossing of a threshold to the last crossing of a threshold can be determined as used to define the level of fibroses. For example, it can be combined with the number of peaks or number of zero crossings to define a level fibroses.

In other embodiments, the amount of waveform fragmentation changing over time is tracked. The change in waveform fragmentation can then be used to determine when fibrosis in the atrial wall is increasing. For example, by tracking a combination of number of peaks, zero crossings and the time from first crossing to last crossing over times, the amount of change in fibrosis can be determined. In many cases detecting changes in these parameters is more indicative of fibroses than detecting specific levels of these parameters.

It should be noted that in some cases the use of multiple electrodes, and the measurement of peaks, zero crossings and/or time from first crossing to last crossing taken from multiple electrodes can be combined together to characterize the total amount of fibrosis in the atrial wall. In general, with multiple electrodes the chance of measuring fibroses at different places in the atrium is larger because the effects of atrial fibroses is greater on the measured potentials when those potentials are measured close to the area containing the fibroses.

As described above, in another embodiment the system and method is used to determine if electrical instability exists in the atrial wall. In this embodiment, the implantable cardiac device evaluates measured waveforms to determine the length of the refractory period in the atrial wall. This allows the implantable cardiac device to detect a shortening of the refractory period that can lead to an increasing likelihood of atrial fibrillation.

In general, the refractory period can be defined as the time period after a stimulation (either evoked or natural) before the heart is electrically ready to be stimulated for the next heartbeat. In most cases the refractory period is characterized by determining the end of the period, i.e., when the heart is electrically ready again. A shortened refractory period is a measure of electrical instability, and as such can lead to an increasing likelihood of atrial fibrillation.

In a first variation on this embodiment, the refractory period can be determined by detecting the atrial T-wave and using the atrial T-wave and digital signal processing to estimate the length of refractory period. In a second variation, the refractory period is measured by detecting the atrial impulse response. In this example, a train of pulses is delivered to the atrium. Capture of the pulses is determined, and used to calculate the refractory period. In both these examples the atrial wall is characterized by determining the length of the refractory period in the atrial wall.

Figure 5:
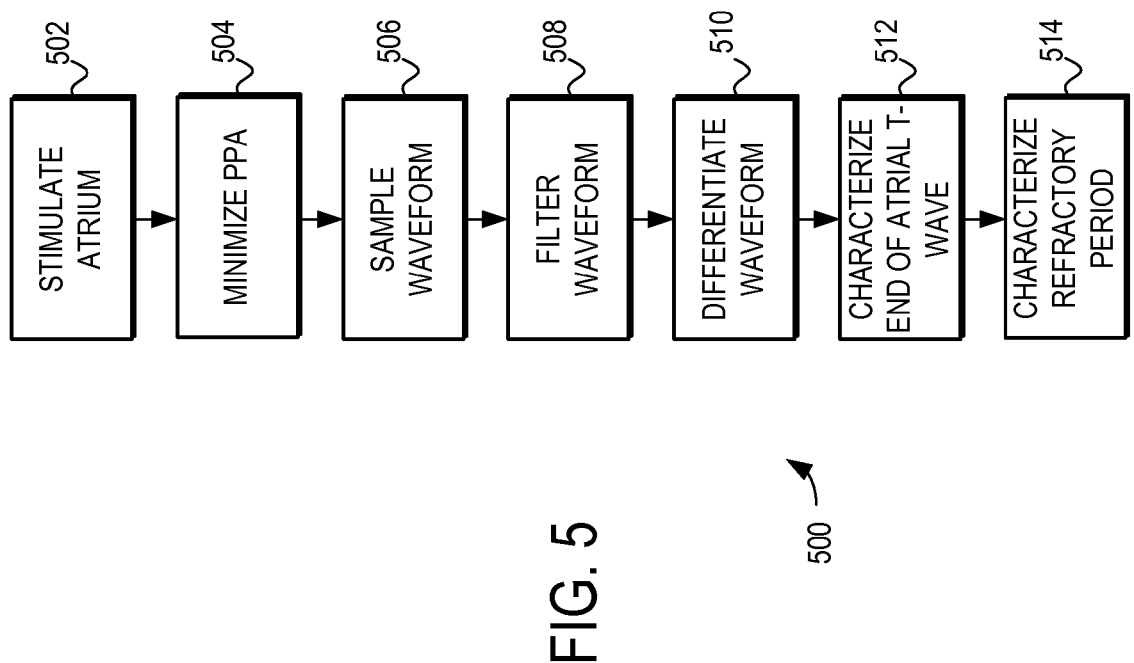
FIG. 5 is a flow diagram of a method for characterizing a refractory period in accordance with an embodiment of the invention.
Figure 6:
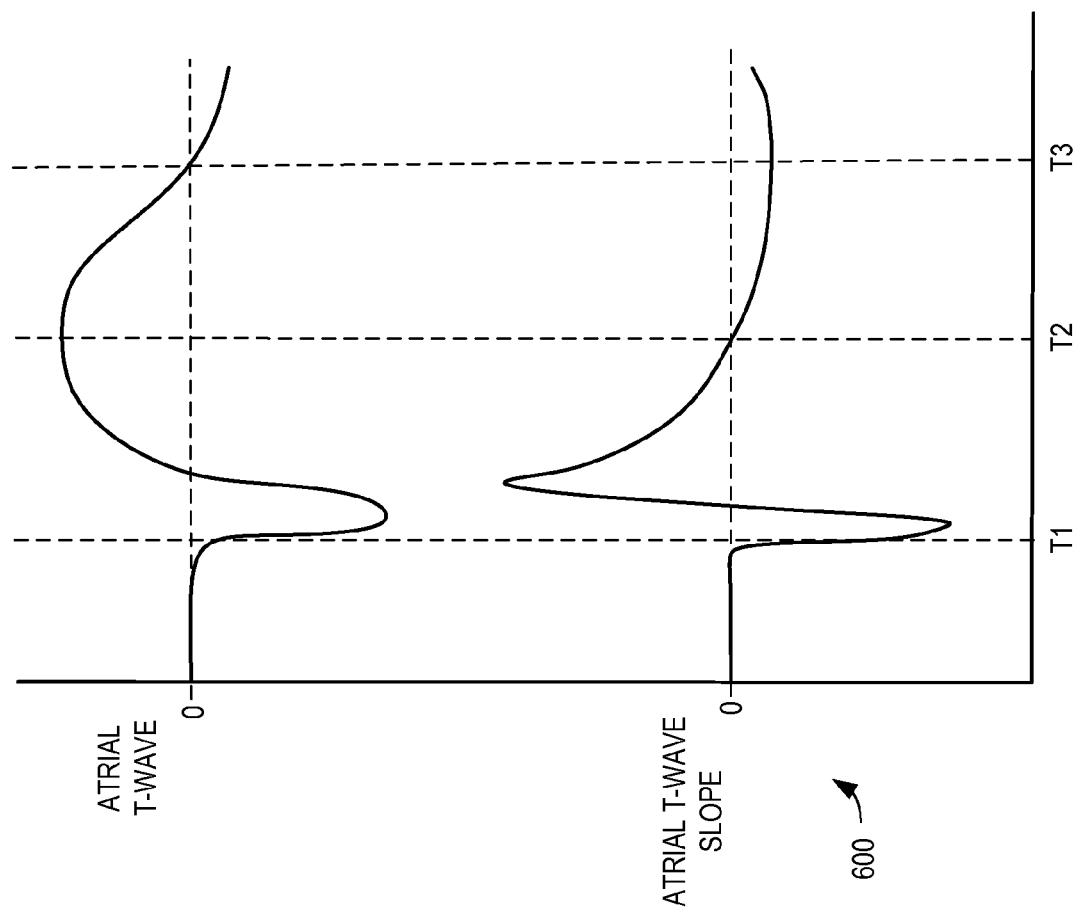
FIG. 6 is a graphical view of an exemplary atrial T-wave and atrial T-wave slope.

Turning now to FIG. 5, a method 500 for characterizing a refractory period in the atrium is illustrated. The method 500 uses a sample atrial T-wave and a calculated slope of the atrial T-wave to characterize the atrial T-wave, and thus characterize the refractory period. Turning briefly to FIG. 6, FIG. 6 includes a graph 600 that illustrates an exemplary sampled and filtered atrial T-wave, and a corresponding atrial T-wave slope. The atrial T-wave begins with a large negative down swing at time T1, followed by a large positive swing that terminates at time T2 and a gentle slope down ward that crosses zero at time T3. The slope of the atrial T-wave follows the corresponding differential pattern. The end of the atrial T-wave, generally considered to occur when the atrial T-wave crosses zero (e.g., time T3) or some other threshold, can be used to characterize the refractory period, and thus can be used to measure electrical instability in the atrial wall. Furthermore, the time at which the slope of the atrial T-wave crosses zero or some other threshold can be used to characterize refractory period. Using the slope has the advantage of reducing the affects of noise on the characterization. This results in a more accurate and consistent characterization of the atrial wall.

Returning to FIG. 5, the first step 502 in method 500 is to stimulate the atrium with a suitable pacing stimulus designed to evoke a heartbeat. A variety of techniques can be used to stimulate the atrium. One example is to use a suitable triphasic pulse. In a triphasic pulse a positive charge is followed by a large negative charge, followed by a second positive charge. These three charges are typically charged balanced to avoid leaving charge at the electrode tip. This helps minimize the post polarization effects.

The next step 504 is to minimize the post-polarization artifact (PPA). The PPA is remaining post-stimulus charge that remains in the electrode after stimulating the atrium. This remaining charge can prevent an accurate reading of the waveforms in the heart. Thus, step 504 minimizes the PPA to facilitate accurate measuring of the atrial waveforms. One technique for reducing the PPA is described in U.S. Pat. No. 6,067,472 entitled "Pacemaker System and Method with Improved Evoked Response and Repolarization Signal Detection" by Bernardus F M. Vonk and Geeske van Oort, and assigned to Medtronic, Inc. In this technique, the PPA is reduced by shortening the post charge time, i.e., the third part of the pacing pulse with positive charge. By doing this and monitoring the resulting polarization this can be minimized to acceptable levels.

With the PPA minimized, the next step 504 is to sample the waveform in the heart. In this step, the implantable medical device electrodes are used to measure the signal in the heart using any suitable technique. As one example, the implantable medical device uses an 8-bit ADC (e.g., ADC 64 of FIG. 2) to sample the waveform at 800 Hz. This provides a digital representation of the atrial T-wave with sufficient resolution to accurately characterize the waveform. Of course, other implantable medical devices can use different data resolutions and data sampling rates. Furthermore, various other processing can be performed in sampling the waveform.

The next step 508 is to filter the sampled atrial T-wave waveform. This can be accomplished using a suitable low pass filter that will remove noise from sampled waveform. When filtering it is important to keep the signal characteristics, and to not induce large phase shifts. Also, in some cases it may be desirable to average several waveforms at this step.

The next step 510 is to differentiate the filtered waveform. This step calculates the slope of the filtered waveform at each point in the waveform. Taken together, this generates the slope of the filtered signal such as was illustrated in FIG. 6. Any suitable digital processing technique can be used to differentiate the waveform. Differentiating the waveform provides improved waveform characterization because the slope of the filtered signal is less affected by noise, and thus can be used to more accurately characterize the atrial T-wave.

The next step 512 is to characterize the end of the atrial T-wave. The end of the atrial T-wave corresponds to the end of refractory period, and thus the end of the atrial T-wave can be used to calculate the refractory period. A variety of different techniques can be used to characterize the end of the atrial T-wave. For example, by comparing the atrial T-wave to a threshold value to determine the time when the atrial T-wave crosses a set value.

As another example, the end of the atrial T-wave can be characterized by comparing the slope of the atrial T-wave to a defined threshold value. For example, the time period between when the atrial T-wave starts (e.g., time T1 in graph 600) and when the slope of the atrial T-wave crosses zero can be used (e.g., time T2). Typically, the time at which the slope of the atrial T-wave crosses zero will be some offset time from the end of the refractory period, which is usually considered to occur closer to when the atrial T-wave crosses zero (e.g., time T3). Thus, by determining when the atrial T-wave slope crosses zero, and using a suitable offset, the end of the atrial T-wave can be estimated. In other cases, the actual end of the atrial T-wave will not need to be estimated precisely. Instead, in cases where only a change in refractory period is needed, the change in the end of the atrial T-wave can be estimated using the changes the time period when the atrial T-wave slope crosses zero. In another embodiment, the threshold value is adjusted to a non-zero value to more accurately characterize the end of the atrial T-wave. Using the slope, rather than the atrial T-wave itself has several advantages. For example, the slope is less likely to be effected by noise in a way that would cause errors in the characterization.

The next step 514 is to characterize the refractory period. A variety of techniques can be used to characterize the refractory period based on the atrial T-waves. As discussed above, in one embodiment changes to the refractory period are tracked over time. A shortening of the refractory period can be indicative of increased electrical instability in the heart. In another embodiment, the end of the refractory period is estimated and compared to a threshold value. Both techniques characterize the refractory period to enable detection of electrical instability and thus characterize the atrial wall. The characterization of the electrical instability can then be used by the implantable medical device in determining appropriate therapies. Additionally, the characterization of the atrial wall can be stored and passed to the clinician using the telemetry system of the implantable medical device.

In a second method, the refractory period is measured by detecting the atrial impulse response. In this example, a train of pulses is delivered to the atrium. Capture of the pulses is determined, and used to calculate the refractory period. In both these examples the atrium wall is characterized by determining the length of the refractory period in the atrial wall.

It should be noted that this is just one example, and different techniques can be used to determine the refractory period. For example, in some cases it may be possible to extract the T-wave from the original signal, and thus eliminate the need to differentiate the measured waveform.

Figure 7:
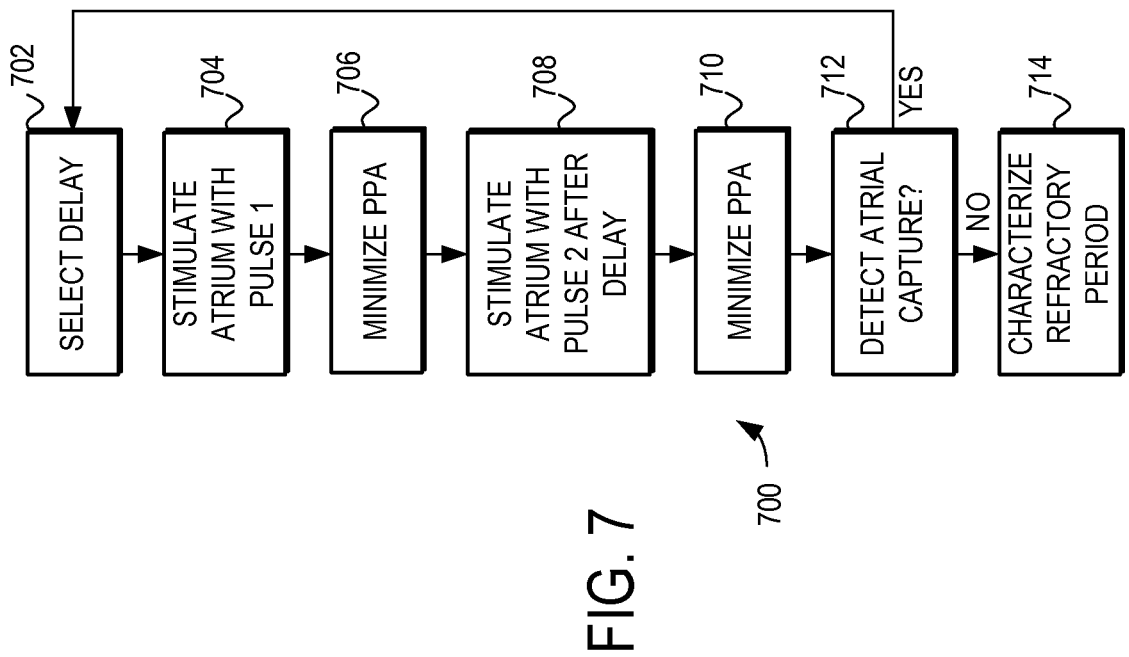
FIG. 7 is a flow diagram of a method for characterizing a refractory period in accordance with an embodiment of the invention.

Turning now to FIG. 7, a second method 700 for characterizing a refractory period in the atrium is illustrated. The method 700 uses a train of pulses delivered to the atrium, with a selected delay between two pulses used to determine the refractory period. Specifically, the delay between pulses is progressively adjusted until a lack of capture is determined. The delay at which capture is lost is then used to characterize the refractory period.

The first step 702 is to select a delay between pulses. Initially, the delay would likely be selected based on past patient history or a default value based on clinical data could be used. After the initial run, the delay would be adjusted to shorten the delay until capture is lost.

The next step 704 is to stimulate the atrium with a suitable pacing stimulus designed to evoke a heartbeat. Again, a variety of techniques and different types of pacing pulses can be used to stimulate the atrium.

The next step 706 is to minimize the post-polarization artifact (PPA). The PPA is again the remaining post-stimulus charge that remains in the electrode after stimulating the atrium. This makes it possible to measure the atrial evoked response. Again, minimizing the PPA can be done using any suitable technique, such as those discussed above.

The next step 708 is to stimulate the atrium with a second suitable pacing stimulus designed to evoke a heartbeat. This second suitable pacing stimulus is done after the stimulation in step 704, with the delay between the first and second pacing stimulus being the delay selected in step 702.

The next step 710 is to again minimize the post-polarization artifact (PPA) using any suitable technique. The next step 712 is to determine if atrial capture has occurred. Atrial capture occurs when the pacing stimulus evokes a heartbeat. Thus, determining if atrial capture has occurred comprises determining if a heart beat has been evoked by the second stimulus. If the second stimulus evokes a heartbeat, then the delay between the first stimulus and the second stimulus is greater than or equal to the refractory period. Conversely, if the delay is less than the refractory period, then the second stimulus will not achieve atrial capture.

A variety of different techniques can be used to detect atrial capture. In one technique, atrial capture is detected by a threshold that the evoked response crosses, or by tracking the amplitude of the evoked response and comparing it to a predetermined number. More information regarding this technique for atrial capture can be found in U.S. Pat. No. 6,067,472.

If atrial capture has occurred, the method 700 returns to step 702. At step 702 a new delay is selected and steps 704-712 are performed again. This process is repeated until the delay is shortened such that atrial capture does not occur. When atrial capture is not detected, the next step 714 is to characterize the refractory period. Specifically, it can be determined with reasonable accuracy that the refractory period is between the longest delay in which atrial capture did not occur and the shortest delay that resulted in atrial capture. Thus, method is able to characterize the refractory period be repeatedly adjusting the delay and performing steps 704-712.

Again, in one variation on this embodiment the calculation of the refractory period is repeated and tracked over time. In another embodiment, the end of the refractory period is estimated and compared to a threshold value. These techniques characterize the refractory period to facilitate detection of electrical instability that is used to characterize the atrial wall. The implantable medical device can then use the characterization of atrial wall to determine appropriate therapies, and can also store and pass this data to a clinician using the medical device's telemetry system.

The present invention thus provides a system and method for characterizing the atrial wall of the heart. The characterization of the atrial wall can be used for a variety of diagnostic and therapeutic purposes. For example, it can be used to detect precursors to various types of hear disease, such as atrial fibrillation. In one embodiment, the system and method is used to determine a likelihood of fibrosis in the atrial wall. In another embodiment, the system and method is used to determine if electrical instability exists in the atrial wall by characterizing the refractory period.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A method of characterizing the atrial wall, the method comprising the steps of:
    sampling an atrial T-wave;
    differentiating the sampled atrial T-wave to calculate the slope of the atrial T-wave; and
    characterizing an end of the atrial T-wave based on the slope of the atrial T-wave; and
    characterizing the atrial wall based on the end of the atrial T-wave.

2. The method of claim 1 wherein the step of characterizing an end of the atrial T-wave based on the slope of the atrial T-wave comprises determining the end of the atrial T-wave by determining when the slope of the atrial T-wave crosses a threshold value.

3. The method of claim 1 wherein the step of characterizing an end of the atrial T-wave based on the slope of the atrial T-wave comprises determining the end of the atrial T-wave by determining when the slope of the atrial T-wave crosses zero.

4. The method of claim 1 wherein the step of characterizing the atrial wall based on the end of the atrial T-wave comprises comparing the end of the atrial T-wave to a previously calculated end of the atrial T-wave to determine a change in the end of the atrial T-wave.

5. A method of characterizing the atrial wall, the method comprising the steps of:
    stimulating an atrium with a first pulse;
    stimulating the atrium with a second pulse, the second pulse occurring a specified delay after the first pulse;
    determining if atrial capture occurs after the second pulse;
    determining the refractory period based on whether atrial capture occurs after the second pulse; and
    characterizing the atrial wall based on the determined refractory period.

6. The method of claim 5 wherein the steps of stimulating an atrium with a first pulse, stimulating the atrium with a second pulse, and determining if atrial capture occurs after the second pulse are repeatedly performed with different specified delays to determine a minimum delay for which atrial capture occurs, and wherein the step of determining the refractory period comprises using the minimum delay to determine the refractory period.

7. The method of claim 5 further comprising the step of minimize post-polarization artifact after the step of stimulating the atrium with a first pulse.

8. An implantable cardiac device, comprising:
    a housing;
    at least one electrode coupled to the housing, the at least one electrode adapted to sample a waveform; and
    a digital signal processor coupled to the housing, the digital signal processor adapted to receive the sampled waveform and determine if electrical instability exists in the atrial wall by measuring a refractory period in the atrial wall, wherein the digital signal processor is adapted to measure the refractory period in the atrial wall by detecting an atrial T-wave and use the atrial T-wave to measure the refractory period in the atrial wall.

9. The implantable cardiac device of claim 8 wherein the digital signal processor is adapted to use the atrial T-wave to measure the refractory period in the atrial wall by using the atrial T-wave to measure the length of the refractory period.

10. The implantable cardiac device of claim 8 wherein the digital signal processor is adapted to measure the refractory period in the atrial wall by delivering a train of pulses to the atrium and determining capture of the train of pulses.

11. The implantable cardiac device of claim 10 wherein the digital signal processor is adapted to determine capture of the train of pulses by shortening the delay between pulses in the train of pulses and determining at which shortened delay capture is lost.

12. An implantable cardiac device, comprising:
   a housing;
   at least one electrode coupled to the housing, the at least one electrode adapted to sample an atrial T-wave; and
   a digital signal processor coupled to the housing, the digital signal processor adapted to:
      determine a refractory period by:
         sampling the atrial T-wave;
         differentiating the sampled atrial T-wave to calculate the slope of the atrial T-wave; and
         characterizing an end of the atrial T-wave based on the slope of the atrial T-wave; and
      characterize the atrial wall based on the determined refractory period.

* * * * *

UNITED STATES PATENT AND TRADEMARK OFFICE
CERTIFICATE OF CORRECTION

| | |
|---|---|
| PATENT NO. | : 7,792,584 B2 |
| APPLICATION NO. | : 11/380113 |
| DATED | : September 7, 2010 |
| INVENTOR(S) | : Geeske Van Oort |

It is certified that error appears in the above-identified patent and that said Letters Patent is hereby corrected as shown below:

Col. 10, line 60, delete "and use the" and insert in place thereof -- and using the --;

Signed and Sealed this
Twenty-eighth Day of December, 2010

David J. Kappos
*Director of the United States Patent and Trademark Office*